United States Patent
Boice et al.

(10) Patent No.: US 10,780,034 B2
(45) Date of Patent: Sep. 22, 2020

(54) COSMETIC COMPOSITIONS CONTAINING QUINONES AND THEIR TOPICAL USE ON SKIN AND HAIR

(71) Applicants: Repairogen Corp, Ithaca, NY (US); University of Louisville Research Foundation, Inc., Louisville, KY (US); Cornell University, Ithaca, NY (US)

(72) Inventors: Michael Boice, San Mateo, CA (US); Frank Borchetta, New Rochelle, NY (US); Albert Cunningham, Crestwood, KY (US); John Trent, Louisville, KY (US); Pengbo Zhou, Princeton Junction, NJ (US); Chenyi Yang, Rego Park, NY (US)

(73) Assignees: REPAIROGEN CORP., Ithaca, NY (US); UNIVERSITY OF LOUISVILLE RESEARCH FOUNDATION, INC., Louisville, KY (US); CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/803,311

(22) Filed: Nov. 3, 2017

(65) Prior Publication Data

US 2018/0116928 A1    May 3, 2018

Related U.S. Application Data

(60) Provisional application No. 62/417,001, filed on Nov. 3, 2016.

(51) Int. Cl.
| | |
|---|---|
| A61K 8/35 | (2006.01) |
| A61Q 19/00 | (2006.01) |
| A61Q 5/00 | (2006.01) |
| A61K 8/49 | (2006.01) |
| A61Q 19/08 | (2006.01) |

(52) U.S. Cl.
CPC ............ *A61K 8/355* (2013.01); *A61K 8/498* (2013.01); *A61Q 5/00* (2013.01); *A61Q 5/002* (2013.01); *A61Q 19/004* (2013.01); *A61Q 19/08* (2013.01)

(58) Field of Classification Search
CPC ...... A61K 8/355; A61Q 19/004; A61Q 19/08; A61Q 5/00; A61Q 5/002
See application file for complete search history.

(56) References Cited

U.S. PATENT DOCUMENTS

| | | |
|---|---|---|
| 6,218,424 B1 | 4/2001 | Hamilton |
| 6,458,974 B1 | 10/2002 | Jiang |
| 6,576,660 B1 | 6/2003 | Liao |
| 7,550,014 B2 | 6/2009 | Greaves |
| 7,910,139 B2 | 3/2011 | Bombardelli |
| 8,029,831 B2 | 10/2011 | Pacioretty |
| 8,137,707 B2 | 3/2012 | Paufique |
| 8,192,767 B2 | 6/2012 | Carta |
| 8,367,121 B2 | 2/2013 | Mazzio |
| 8,501,250 B2 | 8/2013 | Ismail |
| 8,513,181 B2 | 8/2013 | Zhou |
| 8,535,740 B2 | 9/2013 | Babish |
| 8,586,629 B2 | 11/2013 | De Groote |
| 8,703,205 B2 | 4/2014 | Alzahrani |
| 8,841,264 B2 | 9/2014 | Raederstorff |
| 8,895,625 B2 | 11/2014 | Alkharfy |
| 8,927,241 B2 | 1/2015 | Ajikumar |
| 9,180,155 B2 | 11/2015 | Babish |
| 2008/0269510 A1 | 10/2008 | Rahman |
| 2010/0009018 A1 | 1/2010 | Paufique |
| 2010/0173024 A1 | 7/2010 | McDaniel |

FOREIGN PATENT DOCUMENTS

| | | |
|---|---|---|
| FR | 2783425 | 3/2000 |
| JP | 2011168554 | 9/2011 |
| KR | 20110115719 | 10/2011 |
| KR | 101094306 | 12/2011 |
| KR | 20150004963 | 1/2015 |
| WO | 2014031759 | 2/2014 |

OTHER PUBLICATIONS

FR2783425 machine translation from the EPO, underlying document published Sep. 17, 1998, p. 1-5.*
International Search Report PCT/US2017/060018 dated Jun. 4, 2018.

* cited by examiner

*Primary Examiner* — Kortney L. Klinkel
(74) *Attorney, Agent, or Firm* — Pabst Patent Group LLP

(57) ABSTRACT

Described are compositions containing quinones that show activity in enhance DNA repair and/or prevent damage to DNA. The quinones are thymoquinone, lapachol, myrtucommulone C, or mixtures thereof, and can be formulated into cosmetic compositions for topical administration to a subject in need thereof. The cosmetic compositions can also include sunscreens, surfactants, sunless tanning agents, desquamation agents, antiperspirants, colorants, preservatives and mixtures; and a cosmetically acceptable carrier. The compositions should find use in methods for treating the signs of ageing in mammals via topical application to the skin or hair of the mammals.

21 Claims, 1 Drawing Sheet

COSMETIC COMPOSITIONS CONTAINING QUINONES AND THEIR TOPICAL USE ON SKIN AND HAIR

CROSS-REFERENCE TO RELATED APPLICATIONS

This application claims priority to U.S. Provisional Application No. 62/417,001, filed in the U.S. Patent and Trademark Office on Nov. 3, 2016, the disclosure of which is incorporated herein by reference in its entirety.

FIELD OF THE INVENTION

The invention is in the field of cosmetic compositions, particularly cosmetic compositions containing skin healing and hair protective quinones, and their topical use in methods improving the appearance of skin.

BACKGROUND OF THE INVENTION

Many cosmetic compositions utilize chemicals that can be harsh, impair and/or irritate the dermal layers and also harm hair. For instance, popular sunscreen agents such as Avobenzone in use have side-effects including contact dermatitis, acne, rash, and inflammation of hair follicles. Keratolytic agents such as alpha hydroxy acids and many retinoids are recognized to sting and inflame skin. Emulsifiers and surfactants, particularly sulfates and sulfonates, withdraw protective oils from the dermis leaving behind cracked skin and redness. Sunless tanners undergo chemical reactions with amino acids of the epidermis. Antiperspirant salts can induce skin inflammation. Colorants amongst which are p-phenylenediamines have been implicated as mutagenic and carcinogenic. Preservatives such as nitrites can convert to N-nitrosoamines which are known carcinogens. In some measure, all the aforementioned materials cause or have potential to cause DNA damage to skin or hair. Various approaches have been used to counteract the damage, particularly agents that repair DNA.

U.S. Pat. No. 8,513,181 B2 (Zhou) describes methods of preventing or treating conditions associated with DNA damage. The methods and compositions focus on substances interfering with activity of the CUL4A ubiquitin ligase bio target.

U.S. Pat. No. 8,535,740 (Babish et al) reports an improved process for recovery of thymoquinone and use thereof in dietary supplements or therapeutics against inflammation related disorders. Other thymoquinone related documents include U.S. Pat. No. 9,180,155 (Babish), U.S. Pat. No. 8,895,625 (Alkarfy), U.S. Pat. No. 8,501,250 (Ismail), U.S. Pat. No. 8,841,264 (Raederstorff), U.S. Pat. No. 8,703,205 (Alzahrani), U.S. Pat. No. 8,586,629 (De Groote), U.S. Pat. No. 8,367,121 (Mazzio), and U.S. Pat. No. 8,029,831 (Pacioretty).

U.S. Pat. No. 7,550,014 (Greaves) reports lapachol in a hair dyeing composition. U.S. Pat. No. 6,576,660 (Liao) describes lapachol in studies using 5-alpha reductase. U.S. Pat. No. 6,458,974 (Jiang) describes a synthesis of lapachol and conversion to beta lapachone.

A series of patents describes bioactivity, processes and compositions related to myrtucommulone. These include U.S. Pat. No. 7,910,139 (Bombardelli), U.S. Pat. No. 8,192,767 (Carta), U.S. Pat. No. 8,137,707 (Paufique), and US 2008/0269510 (Rahman).

Nonetheless, there remains a need to develop compositions that prevent damage to DNA, skin, hair or a combination thereof, caused by components of cosmetic formulations.

Therefore, it is an object of the invention to provide compositions that inhibit damage to DNA, skin, hair, or a combination thereof.

SUMMARY OF THE INVENTION

Described herein are compositions containing quinones that show activity in preventing damage to DNA and/or enhance DNA repair. In some forms, the quinones are present in an effective amount to inhibit cullin 4A (CUL4A) ubiquitin ligase. In some forms, the quinones constitute from 0.001% to 50% by weight of the composition, preferably, between 0.001 to 10% by weight of the composition. Preferably, the quinones are thymoquinone, lapachol, myrtucommulone C, or a combination thereof. The quinones can be formulated into cosmetic compositions for topical administration to a subject. In some forms, the cosmetic composition also includes sunscreens, surfactants, sunless tanning agents, desquamation agents, antiperspirants, colorants, preservatives, or mixtures thereof, preferably in amounts ranging from 0.1% to 50% by weight of the composition. In some forms, the cosmetic composition also includes a cosmetically acceptable carrier.

Also described are methods for treating the signs of ageing in mammals including topically applying to the skin or hair of the mammals a composition containing the quinones describe herein. Preferably, the composition is a cosmetic composition.

DETAILED DESCRIPTION OF THE INVENTION

I. Definitions

Figure 1A:
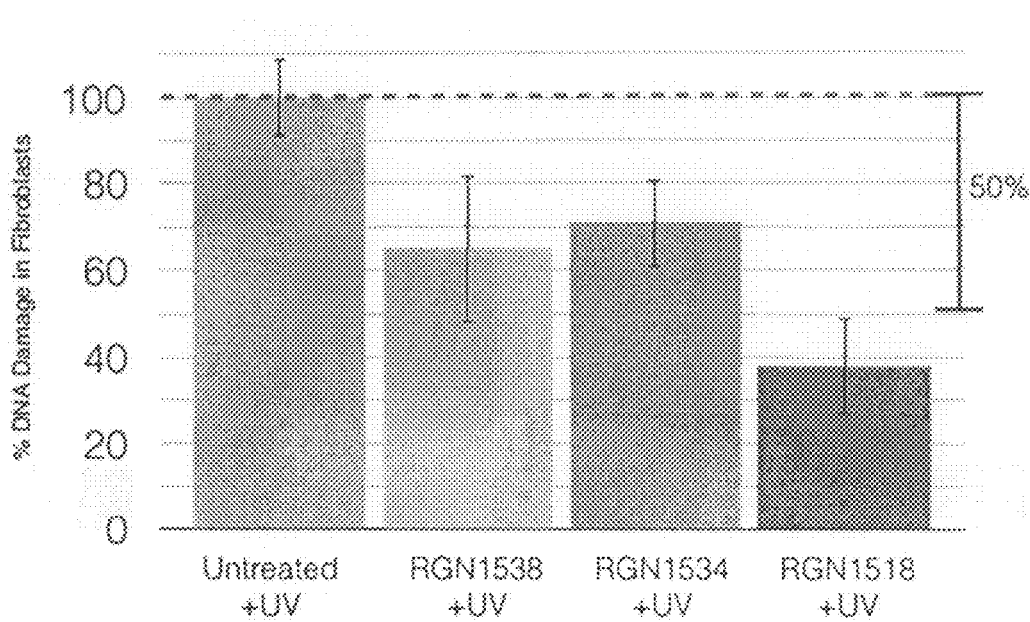
FIGS. 1A and 1B are column charts showing the effects of three compounds, compared to controls, on percent DNA damage by ultraviolet (UV) exposure in fibroblasts (FIG. 1A) and keratinocytes (FIG. 1B). Data are shown as mean±SD (n=3). The compounds are indicated as follows: RGN1518, myrtucommulone C; RGN1534, thymoquinone; and RGN1538, lapachol.
Figure 1B:
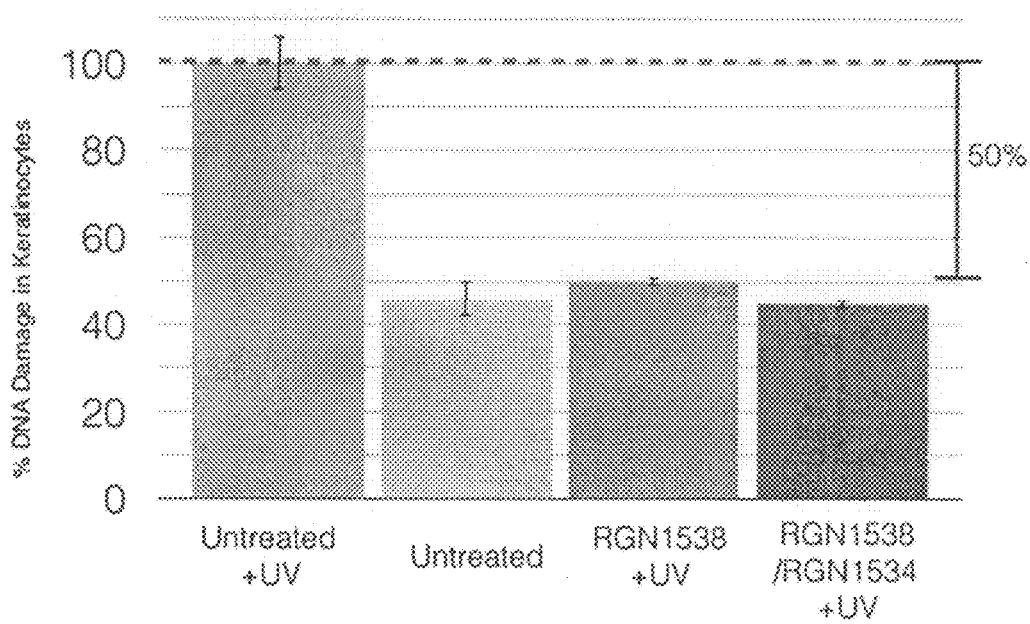

"Cosmetic composition" as used herein, refers to a composition for topical application to skin or hair of mammals, especially humans. Such a composition may be generally classified as leave-on or rinse off, and includes any product applied to a human body for improving appearance, cleansing, odor control or general aesthetics.

"Derivative" as relates to a given compound, refers to another compound that is structurally similar, functionally similar, or both, to the specified compound. Structural similarity can be determined using any criterion known in the art, such as the Tanimoto coefficient that provides a quantitative measure of similarity between two compounds based on their molecular descriptors. Preferably, the molecular descriptors are 2D properties such as fingerprints, topological indices, and maximum common substructures, or 3D properties such as overall shape, and molecular fields. Tanimoto coefficients range between zero and one, inclusive, for dissimilar and identical pairs of molecules, respectively. A compound can be considered a derivative of a specified compound, if it has a Tanimoto coefficient with the specified compound between 0.5 and 1.0, inclusive, preferably between 0.7 and 1.0, inclusive, most preferably between 0.85 and 1.0, inclusive. A compound is functionally similar to a specified compound, if it induces the same pharmacological effect, physiological effect, or both, as the specified compound. "Derivative" can also refer to a modification including, but not limited to, hydrolysis, reduction, or oxidation products, of the disclosed compounds. Hydrolysis, reduction, and oxidation reactions are known in the art.

"Effective amount" and "therapeutically effective amount," used interchangeably, as applied to the nanoparticles, therapeutic agents, and pharmaceutical compositions described herein, mean the quantity necessary to render the desired therapeutic result. For example, an effective amount is a level effective to treat, cure, or alleviate the symptoms of a disease for which the composition and/or therapeutic agent, or pharmaceutical composition, is/are being administered. Amounts effective for the particular therapeutic goal sought will depend upon a variety of factors including the disease being treated and its severity and/or stage of development/progression; the bioavailability and activity of the specific compound and/or antineoplastic, or pharmaceutical composition, used; the route or method of administration and introduction site on the subject; the rate of clearance of the specific composition and other pharmacokinetic properties; the duration of treatment; inoculation regimen; drugs used in combination or coincident with the specific composition; the age, body weight, sex, diet, physiology and general health of the subject being treated; and like factors well known to one of skill in the relevant scientific art. Some variation in dosage will necessarily occur depending upon the condition of the subject being treated, and the physician or other individual administering treatment will, in any event, determine the appropriate dosage for an individual patient.

The terms "inhibit" and "reduce" means to reduce or decrease in activity or expression. This can be a complete inhibition or reduction of activity or expression, or a partial inhibition or reduction. Inhibition or reduction can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "substantially free," describes a composition that has an amount of a component that is at most 10% by weight of the total weight of the sample, as measured an analytical method such as nuclear magnetic resonance spectroscopy. Useful examples of "substantially free" include less than 5% by weight, less than 4% by weight, less than 3% by weight, less than 2% by weight, less than 1% by weight, less than 0.5% wt/wt, less than 0.1% wt/wt, or 0% wt/wt of the sample.

The term "volatile" as used herein refers to those materials which have a measurable vapor pressure at ambient temperature.

"Substituted" refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Alkyl," as used herein, refers to the radical of saturated aliphatic groups, including straight-chain alkyl groups, branched-chain alkyl, cycloalkyl (alicyclic), alkyl substituted cycloalkyl groups, and cycloalkyl substituted alkyl. In preferred forms, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

Preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred forms, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —NO$_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —CF$_3$, —CH$_2$—CF$_3$, —CCl$_3$); —CN; —NCOCOCH$_2$CH$_2$; —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

The terms "alkoxyl" or "alkoxy," "aroxy" or "aryloxy," generally describe compounds represented by the formula —OR', wherein R' includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O—alkynyl. The term alkoxy also includes cycloalkyl, heterocyclyl, cycloalkenyl, heterocycloalkenyl, and arylalkyl having an oxygen radical attached to at least one of the carbon atoms, as valency permits. A "lower alkoxy" group is an alkoxy group containing from one to six carbon atoms.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkenyl" as used herein is a hydrocarbon group of from 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl" as used herein is any $C_5$-$C_{26}$ carbon-based aromatic group, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as CF$_3$, —CH$_2$—CF$_3$, —CCl$_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

"Carbonyl," as used herein, is art-recognized and includes such moieties as can be represented by the general formula:

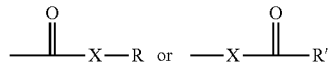

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —$(CH_2)_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

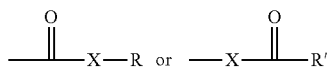

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for the formula

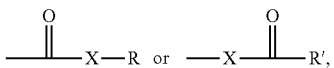

and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred forms, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenoxy" is art recognized, and refers to a compound of the formula —$OR^v$ wherein $R^v$ is (i.e., —O—$C_6H_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—$C_6H_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "amide" or "amido" are used interchangeably, refer to both "unsubstituted amido" and "substituted amido" and are represented by the general formula:

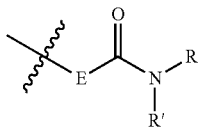

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide. In preferred forms, R and R' each independently represent a hydrogen atom, substituted or unsubstituted alkyl, substituted or unsubstituted alkenyl, or —$(CH_2)_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

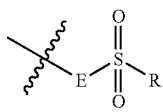

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

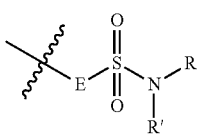

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide.

The term "phosphonyl" is represented by the formula

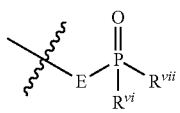

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phosphonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. When two or more heteroaryls are involved, the chemical moiety can be referred to as a "polyheteroaryl."

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. When two or more heteroaryls are involved, the chemical moiety can be referred to as a "substituted polyheteroaryl."

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "urethane" as used herein is represented by the formula —OC(O)NRR', where R and R' can be, independently, hydrogen, an alkyl, alkenyl, alkynyl, aryl, aralkyl, cycloalkyl, halogenated alkyl, or heterocycloalkyl group described above.

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —$NO_2$.

The term "phosphate" refers to —O—$PO_3$.

The term "azide" or "azido" are used interchangeably to refer to —$N_3$.

The term "substituted $C_1$-$C_x$ alkyl" refers to alkyl groups having from one to x carbon atoms, wherein at least one carbon atom is substituted, wherein "x" is an integer from one to ten. The term "unsubstituted $C_1$-$C_x$ alkyl" refers to alkyl groups having from one to x carbon atoms that are not substituted, wherein "x" is an integer from one to ten.

The term "substituted $C_2$-$C_x$ alkenyl" refers to alkenyl groups having from two to x carbon atoms, wherein at least one carbon atom is substituted, wherein "x" is an integer from two to ten. The term "unsubstituted $C_2$-$C_x$ alkenyl" refers to alkenyl groups having from two to x carbon atoms that are not substituted, wherein "x" is an integer from two to ten.

The term "substituted $C_1$-$C_x$ carbonyl" refers to carbonyl groups having from one to x carbon atoms, wherein at least one carbon atom is substituted, wherein "x" is an integer from one to ten. The term "unsubstituted $C_1$-$C_x$ carbonyl" refers to carbonyl groups having from one to x carbon atoms that are not substituted, wherein "x" is an integer from one to ten.

II. Composition

Many components found in cosmetic compositions damage skin and hair. Amongst these components are certain types of sunscreens, thickeners, surfactants, sunless tanners, desquamation agents, antiperspirants, colorants, preservatives and mixtures thereof. Some of these damage involves damage to DNA.

It is now been found that certain quinones have activity in avoiding and repairing damage to DNA, in particular mammalian DNA. Accordingly, the quinones can be used to treat conditions involving DNA damage or used to enhance DNA repair. Described herein, are compositions containing the quinones. In some forms, the compositions are formulated into cosmetic compositions. Preferably, the cosmetic compositions minimize damage caused by the aforementioned components. In some forms, the cosmetic compositions can also contain a cosmetically acceptable carrier such as water; emollients; hydrocarbons; fatty acids; fatty alcohols; humectants; skin lighteners; active peptides; vitamins; additional materials such as resveratrol, etc.; or combinations thereof.

In some forms, the quinone(s) is present in the composition in an effective amount to inhibit cullin 4A (CUL4A) ubiquitin ligase activity, as measured using an assay that measures DNA damage in a cell, in terms of the formation of cyclobutane pyrimidine dimers in DNA. In some forms, the quinone is present in an effective amount to enhance DNA repair. Exemplary assays to measure CUL4A inhibition or enhancement of DNA repair are described below in Example 1.

Advantageously, UV irradiated samples of the quinone or cosmetic compositions formulated with the quinone exhibit, in testing against the CUL4 bio target, a reduction in DNA damage relative to a UV irradiated control of at least 10%, preferably at least 50%, and more preferably by at least 80% over baseline compared to a no treatment control for example, DMSO as measured by % CPD (Cyclobutane Pyrimidine Dimer) formed in a test cell. In most preferred embodiments the inhibition is between 80% and 120%, for example, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 115%, 118%, and 120%. Accordingly, the compositions should be useful in DNA repair, particularly in skin cells.

In some forms, the cosmetic composition does not contain a pharmaceutical grade methionine, an extract from cranberry, cranberry juice, or a combination thereof.

In some forms, besides quinones described herein, the cosmetic composition is substantially free of one or more additional essential oil components extracted from the seed of *Nigella sativa*. For example, the disclosed compositions use pure Thymoquinone and include less 5% by weight, less than 4% by weight, less than 3% by weight, less than 2% by weight, less than 1% by weight, less than 0.5% wt/wt, less than 0.1% wt/wt, or 0% wt/wt of essential oil components extracted from the seed of *Nigella sativa*, which are invariably are included in supercritical fluid extracts of *Nigella sativa*, for example, supercritical $CO_2$ extract of *Nigella sativa* seed. Accordingly, in some forms, the thymoquinone in the disclosed formulations is not a supercritical $CO_2$ extract of *Nigella sativa* seed.

In some forms, the cosmetic composition is substantially free of a phenylethanoid, such as hydroxytyrosol.

In some forms, the cosmetic composition is substantially free of a honey and/or myrth, zinc/zinc supplementation, pyruvate, succinate, alpha-ketoglutarate, oxaloacetate, niacin, fruit extract.

A. Compounds

The compositions contain quinones that have the structural formulae shown below:

Formula I

Formula II

Formula III wherein X and Y are independently carbon (C) or CH; Z is hydroxyl or oxygen; and the dashed line between X and Y, and between Y and Z shows the presence or absence of a bond, depending on the valency of X, Y, and Z;

wherein R1, R2, R3, R4, R5, R6, R7, and R8 are independently hydrogen, unsubstituted C1-C10 alkyl, substituted C1-C10 alkyl, unsubstituted C2-C10 alkenyl, substituted C2-C10 alkenyl, hydroxyl, thiol, halogen, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic;

wherein R9, R10, R11, R12, R13, R14, R15, R16, R17, R18, R19, R20, R21, R22, and R23 are independently hydrogen, unsubstituted C1-C10 alkyl, substituted C1-C10 alkyl, hydroxyl, =O, substituted C1-C10 carbonyl, or unsubstituted C1-C10 carbonyl, thiol, halogen, aryl, substituted aryl, heteroaryl, substituted heteroaryl, alkoxy, substituted alkoxy, aroxy, substituted aroxy, alkylthio, substituted alkylthio, arylthio, substituted arylthio, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic.

In some forms of Formula I, R2 is not hydroxyl. In some forms of Formula I, R4 is not hydroxyl. In some forms of Formula I, R2 and R4 are not hydroxyl. In some forms of Formula I, R1 is not undecyl. In some forms of Formula I, R1 is not undecyl, and R2 and R4 are not hydroxyl. In some forms, the compound of Formula I is not 2,5-dihydroxy-3-undecyl-2,5-cyclohexadiene-1,4-dione.

In some forms of Formula I, R2 and R4 are each hydrogen.

In some forms of Formula I, R1 and R3 are independently unsubstituted C1-C10 alkyl, or substituted C1-C10 alkyl.

In some forms of Formula I, R1 and R3 are independently unsubstituted C1-C5 alkyl, or substituted C1-C5 alkyl; R2 and R4 are each hydrogen.

In some forms of Formula I, R1 is substituted C1-C5 alkyl; R3 is methyl, and R2 and R4 are each hydrogen.

In some forms of Formula II, R5, R6, R7, and R8 are independently hydrogen, C1-C10 alkyl, or substituted C1-C10 alkyl.

In some forms of Formula II, R5, R6, R7, and R8 are hydrogen.

In some forms of Formula II, R1 and R2 are independently unsubstituted C2-C10 alkenyl, substituted C2-C10 alkenyl, C1-C10 alkyl, substituted C1-C10 alkyl, or hydroxyl.

In some forms of Formula II, R1 and R2 are independently unsubstituted C2-C10 alkenyl, substituted C2-C10 alkenyl, or hydroxyl.

In some forms of Formula II, R5, R6, R7, and R8 are independently hydrogen, C1-C10 alkyl, or substituted C1-C10 alkyl; R1 and R2 are independently unsubstituted C2-C10 alkenyl, substituted C2-C10 alkenyl, C1-C10 alkyl, substituted C1-C10 alkyl, or hydroxyl.

In some forms of Formula II, R5, R6, R7, and R8 are hydrogen; R1 and R2 are independently unsubstituted C2-C10 alkenyl, substituted C2-C10 alkenyl, C1-C10 alkyl, substituted C1-C10 alkyl, or hydroxyl.

In some forms of Formula II, R5, R6, R7, and R8 are hydrogen; R1 and R2 are independently unsubstituted C2-C10 alkenyl, substituted C2-C10 alkenyl, or hydroxyl.

In some forms of Formula II, R5, R6, R7, and R8 are hydrogen; R1 is substituted C2-C10 alkenyl, and R2 is hydroxyl.

In some forms of Formula III, R9 is substituted C1-C10 carbonyl.

In some forms of Formula III, R10 is hydroxyl.

In some forms of Formula III, X is carbon (C) or CH, Y is carbon (C), Z is hydroxyl, the dashed line between X and Y is a bond, and the dashed line between Y and Z is absent.

In some forms of Formula III, R11, R12, R13, R14, R15, R16, R18, R19, R20, R21, R22, and R23 are independently hydrogen, substituted C1-C10 alkyl, or unsubstituted C1-C10 alkyl.

In some forms of Formula III, R11, R12, R13, R14, R20, R21, R22, and R23 are unsubstituted C1-C10 alkyl.

In some forms of Formula III, R15, R16, R18, and R19 are independently hydrogen or substituted C1-C10 alkyl.

In some forms of Formula III, R15 and R18 are hydrogen, and R16 and R19 are substituted C1-C10 alkyl.

In some forms of Formula III, R17 is hydroxyl.

In some forms of Formula III, R9 is substituted C1-C10 carbonyl; X and Y are carbon (C), Z is hydroxyl, the dashed line between X and Y is a bond, and the dashed line between Y and Z is absent; R10 is hydroxyl; R11, R12, R13, R14, R20, R21, R22, and R23 are unsubstituted C1-C10 alkyl; R15, R16, R18, and R19 are independently hydrogen or substituted C1-C10 alkyl; and R17 is hydroxyl.

In some forms of Formula III, R9 is substituted C1-C10 carbonyl; X and Y are carbon (C), Z is hydroxyl, the dashed line between X and Y is a bond, and the dashed line between Y and Z is absent; R10 is hydroxyl; R11, R12, R13, R14, R20, R21, R22, and R23 are unsubstituted C1-C10 alkyl; R15 and R18 are hydrogen, R16 and R19 are substituted C1-C10 alkyl; and R17 is hydroxyl.

In some forms of Formula III, R9 is substituted C1-C5 carbonyl; X and Y are carbon (C), Z is hydroxyl, the dashed line between X and Y is a bond, and the dashed line between Y and Z is absent; R10 is hydroxyl; R11, R12, R13, R14, R20, R21, R22, and R23 are unsubstituted C1-C5 alkyl; R15 and R18 are hydrogen, R16 and R19 are substituted C1-C5 alkyl; and R17 is hydroxyl.

In some forms of Formula III, R9 is substituted C1-C5 carbonyl; X and Y are carbon (C), Z is hydroxyl, the dashed line between X and Y is a bond, and the dashed line between Y and Z is absent; R10 is hydroxyl; R11, R12, R13, R14, R20, R21, R22, and R23 are methyl; R15 and R18 are hydrogen, R16 and R19 are substituted C1-C5 alkyl; and R17 is hydroxyl.

In some forms of Formula III, R9 is substituted C1-C5 carbonyl; X and Y are carbon (C), Z is hydroxyl, the dashed line between X and Y is a bond, and the dashed line between Y and Z is absent; R10 is hydroxyl; R11, R12, R13, R14, R20, R21, R22, and R23 are methyl; R15 and R18 are hydrogen, R16 and R19 are isopropyl; and R17 is hydroxyl.

Preferred compounds include the following quinones: thymoquinone, lapachol and myrtucommulone C.

Amounts of the quinones may range from 0.001% to 50% by weight, 0.1% to 50% by weight, from 0.001% to 20% by weight sometimes from 0.001% to 10% by weight, occasionally from 0.001% to 2% by weight, from 0.001% to 1% by weight, 0.001% to 7.5% by weight, or 0.01% to 5.0% by weight of the cosmetic composition. Exemplary percent compositions include 0.01% by weight, 0.024% by weight, 0.10% by weight, 0.25% by weight, 1.0% by weight, 1.50% by weight, 2.00% by weight, 2.5% by weight, and 5.0% by weight of the composition. When combinations of quinones are utilized, their relative weight amounts may range from 1000:1 to 1:1000, occasionally from 100:1 to 1:100, and even from 10:1 to 1:10. In some forms, the relative weight amounts are the same. For example, when two quinones are present the relative weight amounts are 1:1; when three quinones are present the relative weight amounts are 1:1:1, etc.

Thymoquinone

In a preferred embodiment, the compound of Formula I is 2-isopropyl-5-methylbenzo-1,4-quinone, commonly known as thymoquinone, and has the structural formula below:

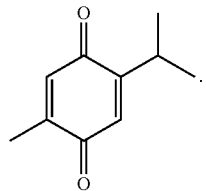

Thymoquinone is a phytochemical compound found in the plant *Nigella Sativa*. Also this material may be found in cultivated *Monarda Fistulosa*.

In a preferred embodiment, the disclosed compositions include thymoquinone monomer or dimer (thymoquinone readily dimerizes to form dithymoquinone. Thymoquinone is included in the formulation in a concentration ranging from 0.01% to 5% by weight, more preferably, between 0.1% and 3% by weight, inclusive.

Lapachol

In some forms, the compound of Formula II is 2-hydroxy-3-(3-methylbut-2-enyl)naphthalene-1,4-dione, commonly known as lapachol, and has the structural formula below:

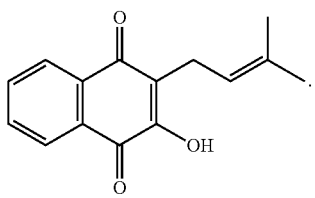 [SMILES: CC(C)=CCC1=C(O)C(=O)c2ccccc2C1=O]

Lapachol is a natural phenolic compound isolated from the bark of the lapacho tree.

In a preferred embodiment, lapachol is included in the formulation in a concentration ranging from 0.01% to 5% by weight, more preferably, between 0.01% and 3% by weight, inclusive. In some embodiments, the lapachol is not encapsulated in water impermeable shell, for example, in a lipid, gelatin, calcium aginate, polymethyl methacrylate urea or other water impermeable shell. In some forms the formulation does not include catechins, for example, epicatechin gallate and epigallocatechin; or rosemary plant extracts.

In some forms, the compound of Formula III, is known by the common name myrtucommulone C, and has the structural formula below:

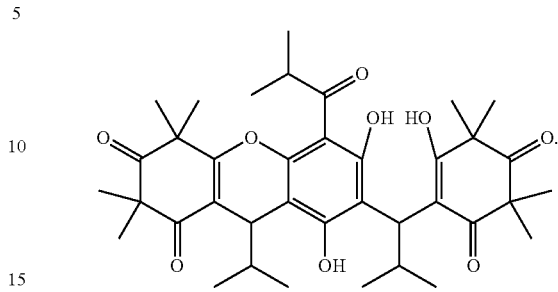

Myrtucommulone is isolated from *Myrtus communis* and is also synthetically available. Among the myrtucommulone family of isomers, stereoisomers and related compounds, is myrtucommulone C which itself occurs as two tautomers (interchangeable constitutional isomers). The chemical structure of myrtucommulone C depicted in its two tautomer interchangeable forms is shown below:

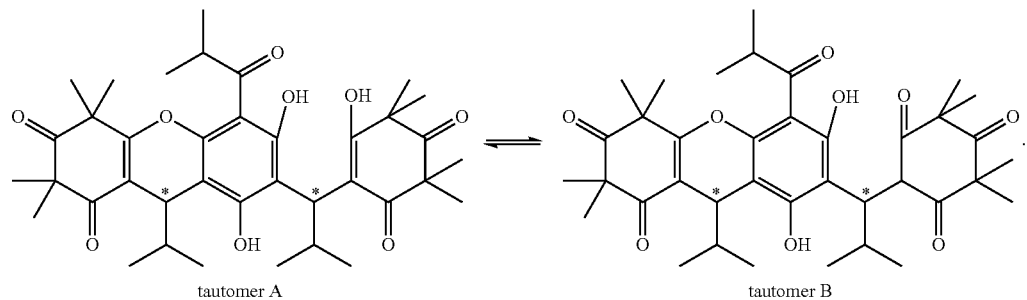

tautomer A          tautomer B

Each of the tautomers has two chiral centers (denoted by the asterisks) where the optical rotation can be either R or S. Therefore, for each tautomer it is possible to have four different compounds with R,R; R,S; S,R; and S,S chirality.

In some preferred embodiment, myrtucommulone C is included in the formulation in a concentration ranging from 0.01% to 5% by weight, more preferably, between 0.01% and 2% by weight, inclusive.

The examples below show that thymoquinone, lapachol, myrtucommulone, and mixtures thereof can function as skin and/or hair protective or healing agents to repair damaged DNA. Among the myrtucommulone isomers, we found myrtucommulone C to be most effective. Combinations of the quinones can be particularly active. For instance, combinations of thymoquinone and lapachol have shown synergistic effect.

B. Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The formulations can include known excipients used in topical formulations, included but not limited to sunscreens, surfactants, preservatives, desquamation agents, antiperspirants, colorants, thickeners, skin lighteners, vitamins and other therapeutically active agents in a cosmetically acceptable carrier.

The cosmetic compositions may be formulated into a wide variety of product types that include, but are not limited to, solutions; suspensions; lotions; creams; gels; toners; sticks; sprays; ointments; cleansing liquid washes; cleansing solid bars; shampoos; hair conditioners; pastes; foams; powders; mousses; shaving creams; wipes; strips; patches (transdermal or non-transdermal); electrically-powered patches; wound dressing and adhesive bandages; hydrogels; film-forming products; facial and skin masks; and make-up such as foundations, eye liners, and eye shadows.

(1) Sunscreens

Sunscreens used herein may be organic or inorganic. They include both UVA and UVB protective ranges. Amounts of sunscreen may range from 0.01% to 20% by weight, 0.1% to 50% by weight, usually from 0.5% to 15% by weight, and often from 4% to 12% by weight of the cosmetic composition.

Organic sunscreens will have at least one chromophoric group absorbing within the ultraviolet ranging from 290 nm to 400 nm. Chromophoric organic sunscreens may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone); Octabenzone; 4-Isopropyldibenzoylmethane; Butylmethoxydibenzoylmethane; Etocrylene; and 4-isopropyldibenzoylmethane).

Particularly important sunscreens are: 2-ethylhexyl p-methoxycinnamate (available as PARSOL MCX®), 4,4'-t-butyl methoxydibenzoylmethane (known commonly as Avobenzone, available as PARSOL 1789®), octylsalicylate (available as DERMABLOCK OS®), tetraphthalylidene dicamphor sulfonic acid (available as MEXORYL SX®), benzophenone-3 (Oxybenzone) and mixtures thereof.

Inorganic sunscreens are usually microfine particles of titanium dioxide and of zinc dioxide. "Microfine" is defined herein as average particle size ranging from 10 nm to 200 nm, usually from 20 nm to 100 nm.

(2) Surfactants

Surfactants suitable for use may be those which can form emulsions and/or association structures. Surfactants can be categorized as being of the anionic, nonionic, cationic, or amphoteric type. The term "surfactants" are defined herein to include materials otherwise called "emulsifiers".

The surfactants can be used at levels from 0.1% to 97% by weight, preferably from 2% to 75% by weight, 0.1% to 50% by weight, more preferably from 10% to 90% by weight, and most preferably from 20% to 70% by weight of the cosmetic composition.

Examples of surfactants which may be used in the compositions described herein include salts of C8-C22 alkyl chain compounds. Representative surfactants include sodium tallowate, sodium cocoate, sodium alkyl sulfate (e.g., sodium lauryl sulfate and sodium myristyl sulfate), sodium N-acyl sarcosinates (e.g., sodium N-lauroyl sarcosinate and sodium N-myristoyl sarcosinate), sodium dodecylbenzenesulfonate, sodium hydrogenated coconut fatty acid monoglyceride sulfate, sodium lauryl sulfoacetate and N-acyl glutamates (e.g., N-palmitoyl glutamate). N-methylacyltaurin sodium salt, N-methylacylalanine sodium salt, sodium alpha-olefin sulfonate and sodium dioctylsulfosuccinate; N-alkylaminoglycerols (e.g., N-lauryl-diamino-ethylglycerol and N-myristyldiaminoethyl glycerol), N-alkyl-N-carboxymethylammonium betaine and sodium 2-alkyl-1-hydroxyethylimidazoline betaine; polyoxyethylenealkyl ether, polyoxyethylene alkylaryl ether, polyoxyethylene lanolin alcohol, polyoxyethylene glyceryl monoaliphatic acid ester, polyoxyethylene sorbitol aliphatic acid ester, polyoxyethylene aliphatic acid ester, higher aliphatic acid glycerol ester, sorbitan aliphatic acid ester, and polyoxyethylenesorbitan aliphatic acid esters such as polyoxyethylenesorbitan monooleate and polyoxyethylene sorbitan monolaurate.

(3) Preservatives

Preservatives may be incorporated into the cosmetic compositions to protect against the growth of potentially harmful microorganisms. Suitable traditional preservatives are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methylchloroisothiazolinone and methylisothiazolinone combinations, phenoxyethanol, methyl paraben, propyl paraben, imidazolidinyl urea, sodium dehydroacetate and benzyl alcohol. Preferred preservatives include phenoxyethanol, ethylhexylglycerine, or a combination thereof. Preservatives may be employed in amounts ranging from 0.01% to 2% by weight of the cosmetic composition. Exemplary percent compositions of the preservative are 0.01%, 0.1%, 0.9%, 1.0%, and 1.5%. In some forms, phenoxyethanol constitutes 0.9% by weight, and ethylhexylglycerine constitutes 0.1% by weight of the composition.

(4) Desquamation Agents

Desquamation agents may be present. Illustrative are the monocarboxylic acids. Monocarboxylic acids may be substituted or unsubstituted with a carbon chain length of up to 16. Particularly preferred carboxylic acids are the alpha-hydroxycarboxylic acids, beta-hydroxycarboxylic or polyhydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic, malic and tartaric acids. A representative salt that is particularly preferred is ammonium lactate. Salicylic acid is representative of the beta-hydroxycarboxylic acids. Amounts of these materials when present may range from 0.1% to 50% by weight, 0.01 to 15% by weight of the cosmetic composition.

Preferred desquamation agents may be selected from the group consisting of glycolic acid, lactic acid, salicylic acid, retinoic acid, retinol and mixtures thereof, and including salt forms thereof.

(5) Antiperspirants

Antiperspirant skin care cosmetic compositions for use herein may include well known antiperspirant metal salts of aluminum, zinc, zirconium and zirconium aluminum mixtures of sulfates, chlorides, chlorohydroxides, tetrachlorohydrex glycinates, alums, formates, lactates, benzyl sulfonates, succinates, phenol sulfonates and the like. Typical levels of antiperspirant metal salts range from 0.1% to 50% by weight, from 1% to 35%, preferably from 1.5% to 25% by weight of the cosmetic composition.

(6) Colorants

Colorants may either be dyes or pigments. A distinction is usually made between a pigment, which is insoluble in its vehicle (resulting in a suspension), and a dye, which either is itself a liquid or is soluble in its vehicle (resulting in a solution). A colorant can act as either a pigment or a dye depending on the vehicle involved. In some cases, a pigment can be manufactured from a dye by precipitating a soluble dye with a metallic salt. The resulting pigment is called a lake pigment.

Among the more common dyes are Alizarin, Azophloxin, Chrysoidin, Congo Red, Fuchsin acid, Gentian violet, Janus green, Methyl Red, Naphthol Green, Naphthol Yellow, Rose Bengal, Sudan II, Titan Yellow and combinations thereof. Amongst pigments, titanium dioxide and aluminum lakes (aluminum salts of dyes) are most common. Amounts of the colorant may, according to the type of cosmetic product (lipstick, foundation, hair dye, etc) range from 0.1% to 50% by weight, 0.01% to 10% by weight, usually from 0.01% to 5% by weight of the cosmetic composition.

(7) Cosmetically Acceptable Carrier

Cosmetic compositions of this invention also include a cosmetically acceptable carrier. Amounts of the carrier may range from 0.1% to 50% by weight, from 1% to 99.9% by weight, preferably from 70% to 95% by weight, most preferably from 80% to 90% by weight of the composition. Among the useful carriers are water, emollients, fatty acids, fatty alcohols, humectants, thickeners, hydrocarbons, and combinations thereof. The carrier may be aqueous, anhydrous, or an emulsion. Preferably the compositions are aqueous, especially water and oil emulsions of the W/O or O/W, or double emulsion, such as the W/O/W variety.

Water when present as carrier or otherwise may advantageously be incorporated into the compositions as a deionized, sterilized or pasteurized liquid or can be heat treated or irradiated after having been mixed with other components of the composition. These treatments insure elimination of pathogenic microbes. Water, when present may be in amounts ranging from 5% to 95% by weight, 8% to 76% by weight, 20% to 70% by weight, or 35 to 60% by weight of the composition. Exemplary percent compositions of water include 9.6% by weight, 13.996% by weight, 21.29% by weight, 21.29% by weight, 32.69% by weight, 60.64% by weight, 71.11% by weight, and 75.05% by weight.

Emollient materials may serve as cosmetically acceptable carriers. These may be in the form of silicone oils, synthetic or natural esters and hydrocarbons. Amounts of the emollients may range anywhere from 0.1% to 95% by weight, from 0.1% to 50% by weight, preferably between 1% and 50% by weight, inclusive, from 1% to 25% by weight, of the cosmetic composition. A preferred emollient is caprylic/capric triglyceride. In some forms the capric/capric triglyceride constitutes about 15% by weight of the cosmetic composition.

Silicone oils may be divided into the volatile and nonvolatile variety. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ m²/s to 0.1 m²/s at 25° C. Among the preferred nonvolatile emollients useful in the present compositions are the polydimethyl siloxanes having viscosities from about $1 \times 10^{-5}$ m²/s to about $4 \times 10{-4}$ m²/s at 25° C.

Another class of nonvolatile silicones are emulsifying and non-emulsifying silicone elastomers. Representative of this category is Dimethicone/Vinyl Dimethicone Crosspolymer available as Dow Corning 9040. General Electric SFE 839, and Shin-Etsu KSG-18. Silicone waxes such as Silwax WS-L (Dimethicone Copolyol Laurate) may also be useful.

Among the ester emollients are: alkyl esters of saturated fatty acids having 10 to 24 carbon atoms. Examples thereof include behenyl neopentanoate, isononyl isonanonoate, isopropyl myristate and octyl stearate; ether-esters such as fatty acid esters of ethoxylated saturated fatty alcohols; polyhydric alcohol esters such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols; wax esters such as beeswax, spermaceti wax and tribehenin wax; and sugar ester of fatty acids such as sucrose polybehenate and sucrose polycottonseedate.

Hydrocarbons which are suitable cosmetically acceptable carriers include petrolatum, mineral oil, $C_{11}$-$C_{13}$ isoparaffins, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol and cetyl alcohol.

Humectants of the polyhydric alcohol-type can be employed as cosmetically acceptable carriers. Typical polyhydric alcohols include glycerol (also known as glycerine), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.1% to 50% by weight, 0.5% to 50% by weight, preferably between 1% and 15% by weight of the composition. In some forms the humectant constitutes about 15% by weight of the composition. In some forms, the humectant is glycerine.

Thickeners can be utilized as part of the cosmetically acceptable carrier of compositions according to the present invention. Typical thickeners include crosslinked acrylates (e.g. CARBOPOL 982®), hydrophobically-modified acrylates (e.g. CARBOPOL 1382®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, and silicates such as magnesium aluminum silicate (VEEGUM®). Amounts of the thickener may range from 0.1% to 50% by weight, 0.001% to 10% by weight, usually from 0.001% to 1% by weight, optimally from 0.01% to 0.5% by weight of the composition. Most preferred thickeners include hydroxyethyl acrylate/sodium acryloyldimethyl taurate copolymer, polyacrylate crosspolymer-6, or a combination thereof. Preferably, the thickeners include hydroxyethyl acrylate/sodium acryloyldimethyl taurate copolymer, and polyacrylate crosspolymer-6. Preferably each of these constitutes about 0.5% by weight of the cosmetic composition.

(8) Additional Materials

Also included may be such materials as resveratrol, alpha-lipoic acid, ellagic acid, kinetin, retinoxytrimethylsilane (available from Clariant Corp. under the SILCARE 1M-75®), dehydroepiandrosterone (DHEA) and combinations thereof. Ceramides (including Ceramide 1. Ceramide 3. Ceramide 3B, Ceramide 6 and Ceramide 7) as well as pseudoceramides are useful. Amounts of these materials may range from 0.1% to 50% by weight, 0.001 to 10% by weight, preferably from 0.01% to 1% by weight of the composition.

The cosmetic compositions may contain an active peptide selected from pentapeptides, derivatives of pentapeptides, and mixtures thereof. As used herein, "pentapeptides" refers to both the naturally occurring pentapeptides and synthesized pentapeptides. A pentapeptide derivative-containing composition is MATRIXYL®, which is commercially available from Sederma, France. The pentapeptides and/or pentapeptide derivatives are preferably included in amounts of from 0.1% to 50% by weight, 0.001% to 20% wt/v.

The cosmetic compositions can include a skin lightening compound. Illustrative substances are placental extract, lactic acid, niacinamide, arbutin, kojic acid, ferulic acid, hydroquinone, resorcinol and derivatives including 4-substituted resorcinols and combinations thereof. Amounts of these substances may range from 0.1% to 10% by weight, preferably from 0.5% to 2% by weight of the composition.

The cosmetic compositions may include vitamins. Illustrative vitamins are Vitamin A (retinol), Vitamin $B_2$, Vitamin $B_3$ (niacinamide). Vitamin $B_6$, Vitamin B12, Vitamin C, Vitamin D, Vitamin E, Vitamin K and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. A particularly suitable Vitamin $B_6$ derivative is Pyridoxine Palmitate. Flavonoids may also be useful, particularly glucosyl hesperidin, rutin, and soy isoflavones (including genistein, daidzein, equol, and their glucosyl derivatives) and mixtures thereof. Total amount of vitamins or flavonoids when present may range from 0.1% to 50% by weight, 0.001% to 10% by weight of the composition.

In some forms, the cosmetic composition contains an emollient selected from those described above; a thickening agent selected from those described above; water, a humectant selected from those described above; a preservative selected from those described above, and any of the quinones defined by Formula I, Formula II, Formula III.

In some forms, the cosmetic composition contains: caprylic/capric triglyceride; hydroxyethyl acrylate/sodium acryloyldimethyl taurate copolymer polyacrylate crosspolymer-6; water glycerin; phenoxyethanol; ethylhexylglycerin; and any of the quinones defined by Formula I, Formula II, or Formula III.

In some forms, the cosmetic composition contains: caprylic/capric triglyceride, 15% by weight; hydroxyethyl acrylate/sodium acryloyldimethyl taurate copolymer, 0.5% by weight; polyacrylate crosspolymer-6, 0.5%, by weight; water, 77.75% by weight; glycerin, 5.0% by weight; phenoxyethanol, 0.9% by weight; ethylhexylglycerin, 0.1% by weight; and lapachol, 0.25% by weight.

In some forms, the cosmetic composition contains: caprylic/capric triglyceride, 15% by weight; hydroxyethyl acrylate/sodium acryloyldimethyl taurate copolymer, 0.5% by weight; polyacrylate crosspolymer-6, 0.5%, by weight; water, 77.90% by weight; glycerin, 5.0% by weight; phenoxyethanol, 0.9% by weight; ethylhexylglycerin, 0.1% by weight; and myrtucommulone C, 0.1% by weight.

III. Methods of Using

The disclosed compositions can be used to inhibit CUL4 ubiquitin ligase in a subject in need thereof. For example the compositions can be administered in conditions involving DNA damage and/or needing DNA repair. In preferred embodiments the cosmetic compositions can be used topically to treat the signs of ageing. These signs include formation of fine lines and wrinkles, inadequate skin firmness, reduction of skin luminescence, lack of skin smoothness, poor skin elasticity, formation of age spots, blotching, sallowness, uneven pigmentation, spider veins (telangiectasia), thinning of hair, lack of hair lustre or shine, hair with split ends and combinations thereof.

Advantageously, UV irradiated samples of the quinone or cosmetic compositions formulated with the quinone exhibit, in testing against the CUL4 bio target, a reduction in DNA damage relative to a UV irradiated control of at least 10%, preferably at least 50%, most preferably by at least 80% over baseline compared to no treatment control, as measured by % CPD (Cyclobutane Pyrimidine Dimer) formed in a test cell. Accordingly, the compositions should be used in DNA repair, particular in skin cells.

Other uses for the presently described quinones are in cosmetic compositions that remediate sunburn as after-care products, that control diaper rash, that clear acne, that treat eczema, inhibit psoriasis, retard dandruff and control itching.

IV. Methods of Making

The cosmetic compositions can be formulated by creating an emulsion containing the components described above, using a cold process formulation method. Such emulsions can be made using cold process polymeric, anionic, bases such as SEPIMAX ZEN®. In some forms, an emollient, such as caprylic/capric triglyceride; a thickening agents, such as hydroxyethyl acrylate/sodium acryloyldimethyl taurate copolymer and polyacrylate crosspolymer-6; water; a humectant, such as glycerin; and preservatives, such as phenoxyethanol and ethylhexylglycerin can be used as base components in making the cosmetic compositions. Any of the quinones described above, can be added to the base components to make the final cosmetic composition. Preferably, the quinones are lapachol, myrtucommulone C, thymoquinone, or a combination.

The cosmetic compositions may also be formulated using formulation methods utilizing different temperatures. Preferably, any of the quinones described above can be added to the base components at temperatures from 0° C. to 50° C. by stirring the components until the quinones have solubilized in the formulation.

Except in the examples, or where otherwise explicitly indicated, all numbers in this description indicating amounts of material or conditions of reaction, physical properties of materials and/or use are to be understood as modified by the word "about." All amounts are by weight of the final cosmetic composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

EXAMPLES

Example 1

Methods

A two-tiered approach was employed to discover novel active ingredients derived from natural sources that have the ability to inhibit the activity of a target protein, cullin 4A CUL4A, and which can be used in cosmetic compositions.

The first tier used an in silico screen and comprehensive computer algorithm to screen a library of over ~150,000 natural products that have the ability to inhibit CUL4A based on their structure and predicted ability to bind to the CUL4A protein and disrupt its activity.

The second tier of screening involved experiments that covered modulating the activity of CUL4A. The top compounds with predicted activity from the first tier were subjected to tests to identify which actives have significant inhibitory activity against CUL4A.

Results

In silico screening of the ~150,000 compounds resulted in a hit rate of approximately 0.36% or 54 active ingredients that passed set comprehensive filters with a high (<88%) predictive inhibitory activity against CUL4A. A BPB-CUL4A AlphaLISA assay was performed using the 54 compounds to determine their CUL4A inhibitory properties in vitro. Next, these 54 leads were tested for their cell-based inhibitory activity against CUL4A. A first cell-based assay involved the inhibition of DNA damage-binding protein 2 (DDB2) degradation in mouse embryonic fibroblast (MEF) cells in vitro. To determine the specificity of the compounds, another cell-based assay was performed to determine the inhibition of IKBa degradation in HeLa cells in vitro. Preferably, the compounds show high DDB2 inhibition and less inhibition of IKBa degradation. IkBa is a target of CUL4B, and this assay provides insight into the specificity of the compounds. These tests led to the selection of three active compounds that passed inhibition and selectivity thresholds and, thus, were suitable for use in cosmetic compositions. These were thymoquinone, lapachol and myrtucommulone C.

Predictive activity against CUL4A was scored from 0-1, with 1 being the highest predictive activity. Outlined below are the results of the in silico predictions.

In Silico Average Predicted Activity

| Compound | Ave. Predicted Activity |
| --- | --- |
| Thymoquinone | 0.936 |
| Lapachol | 0.910 |
| Myrtucommulone C | 0.895 |

The Table below reports the ability of compounds to disrupt CUL4A activity in vitro (in a cell free CUL4 inhibition assay) ascertained from the BPB-CUL4A AlphaLISA assay. Activity above 30% was set to distinguish true hits from false positives.

In Vitro Inhibition Results

| Compound | % Inhibitory Activity |
| --- | --- |
| Thymoquinone | 70.4% |
| Lapachol | 34.4% |
| Myrtucommulone C | 48.9% |

In a further Table below are reported in vitro cell based results displayed as a percentage increased inhibition of CUL4A over baseline compared to a no treatment control i.e., DMSO.

In Vitro Cell Based Assay

| Compound | % Inhibit |
| --- | --- |
| Thymoquinone | 85% |
| Lapachol | 80% |
| Myrtucommulone C | 115% |

In this cell-based assay, the % is DDB2 (DNA binding degradation protein 2) remaining after UV treatment over baseline compared to a control group. In the DMSO control group, the DDB2 remaining % was between 20-30%.

Lastly, tests were conducted on human skin cells. The testing was performed using neonatal foreskin keratinocytes, a type of skin cell that is a common model for skin testing across the cosmetic industry. The skin cells were purchased from Thermo Fisher Scientific Co. (NY) and grown in Dulbecco Modified Eagle Medium (DMEM) supplemented with 10% Fetal Bovine Serum (Thermo Fisher Scientific). Cultures were maintained at 37° C. within an air atmosphere of 5% carbon dioxide and about 95% humidity.

The skin cells were seeded in 12-well plates and incubated for 24 hours. After incubation, the cells were washed in phenyl benzene sulfonate (PBS) and irradiated with UVB at a dosage of 35 mJ/cm$^2$ using a Viber Lourmat BIO-Sun System (Marne-la-Vallee, France). The test compounds and control materials were added to the medium immediately following UVB irradiation; the treated mediums were allowed to continue for 12 hours at 37° C. under the air atmosphere with 5% carbon dioxide at about 95% humidity. In parallel, each test compound was added to non-irradiated cells as baseline controls. Untreated cells were used as negative controls. All treatments were performed in triplicate.

Dosage levels for samples were 12.5 microMolar except lapachol dosed at 3 microMolar. Following incubation, the cells were washed with PBS, collected and stored at −80° C.

DNA was extracted from the collected cells using a QIAamp Blood Kit (QIAGEN, CA, USA) in accordance with the manufacturer's protocol. The amounts of cyclobutane pyrimidine dimers (CPDs) in the various samples were determined by the CPD ELISA protocol. In accordance with this protocol, an OXISELECT® UV-Induced DNA Damage ELISA Kit (Cell Biolabs Inc., CA, USA) was employed for the testing done in accordance with the manufacturer's instructions. Amounts of CPD in UVB-treated samples were determined in percentage relative to the value of untreated fibroblasts. The greater the measured % CPD, the greater the DNA damage. Thus, in the Table below, the smaller the "Avg (% Untreated)" value, the better is the UVB damage induced inhibitory effect.

Mean standard deviation comparisons between data groups employed the GraphPad Prism 6.05 software (GraphPad Software, CA, USA). Statistical analysis was performed using ANOVA with Holm-Sidak's test or unpaired t-test with Welch's correction.

Results of the human fibroblast cell assay are recorded in the Table below. Therein is shown the significant DNA damage inhibitory effect of lapachol, thymoquinone and myrtucommulone C, with the latter being the most effective inhibitor.

Human Fibroblast Cell Assay

| Test Sample or Control | Avg (% Untreated) | St Dev |
| --- | --- | --- |
| Untreated Control (no UVB) | 99.2 | 12.59 |
| Untreated Control (UVB) | 3907 | 423.1 |
| Niacinamide | 2216 | 64.4 |
| Lapachol | 2076 | 127.2 |
| Thymoquinone | 2554 | 252 |
| Myrtucommulone C | 1362 | 307.8 |

In summary, the activity of the compounds has been tested in three different phases: the computer screen, an in vitro assay designed to specifically detect CUL4A inhibition, and also lastly in a biological setting having activity in cells.

Example 2

An illustrative skin care product including thymoquinone for treating age spots and lightening skin has the formula below.

| Component | Weight % |
| --- | --- |
| Thymoquinone | 0.10 |
| Niacinamide | 4.00 |
| Isohexadecane | 3.00 |
| Isopropyl isostearate | 2.00 |

-continued

| Component | Weight % |
| --- | --- |
| Sucrose Polycottonseedate | 0.70 |
| Polymethylsilsesquioxane | 0.25 |
| Cetearyl Glucoside/Cetearyl Alcohol | 0.25 |
| Behenyl Alcohol | 0.40 |
| Ethyl Paraben | 0.20 |
| Propyl Paraben | 0.10 |
| Cetyl Alcohol | 0.30 |
| Stearyl Alcohol | 0.45 |
| PEG-100 Stearate | 0.10 |
| Glycerin | 8.50 |
| Titanium Dioxide | 0.60 |
| Polymethacrylate | 2.00 |
| Dimethicone/Dimethiconol | 2.00 |
| Water | to 100 |

The water phase components are combined in a suitable vessel and heated to 75° C. In a separate suitable vessel, combine the oil phase ingredients and heat to 75° C. Next add the oil phase to the water phase and mill the resulting emulsion (e.g., with a Tekmar™ T-25 mill). Then, add the thickener to the emulsion and cool the emulsion to 45° C. while stirring. At 45° C., add the remaining components. Cool the product and stir to 30° C. and pour into suitable containers.

Example 3

A representative skin care composition incorporating Lapachol in the form of a cosmetic lotion is outlined below:

| Component | Weight % |
| --- | --- |
| Water | Balance |
| Disodium EDTA | 0.05 |
| Methyl Paraben | 0.15 |
| Magnesium Aluminum Silicate | 0.60 |
| Triethanolamine | 1.20 |
| Xanthan Gum | 0.20 |
| Natrosol ® 250HHR (ethyl cellulose) | 0.50 |
| Butylene Glycol | 3.00 |
| Glycerin | 2.00 |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Lapachol | 0.25 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| (Isotridecyloxy)propionic acid (branched) or (Isotridecyloxy)acetic acid (branched) | 2.00 |
| Vitamin A Palmitate | 0.10 |
| Bisabolol | 0.01 |
| Vitamin A Acetate | 0.01 |
| Fragrance (20% Limonene and 3% gamma terpinene) | 0.03 |
| Retinol 50C | 0.02 |

Example 4

A water-in-oil topical liquid make-up foundation incorporating Lapachol is described below.

| Component | Weight % |
|---|---|
| Lapachol | 2.00 |
| Cyclomethicone | 9.25 |
| Oleyl Oleate | 2.00 |
| Dimethicone Copolyol | 20.00 |
| Talc | 3.38 |
| Pigment (Iron Oxides) | 10.51 |
| Spheron L-1500 (Silica) | 0.50 |
| Synthetic Wax | 0.10 |
| Arachidyl Behenate | 0.30 |
| Cyclomethicone | 1.00 |
| Trihydroxystearin | 0.30 |
| Laureth-7 | 0.50 |
| Propyl Paraben | 0.25 |
| Perfume | 0.10 |
| Methyl Paraben | 0.12 |
| Propylene Glycol | 8.00 |
| Niacinamide | 4.00 |
| Glycerin | 3.00 |
| Sodium Chloride | 2.00 |
| Water | To 100 |

Example 5

An aerosol packaged foaming cleanser is outlined fortified with myrtucommulone C.

| Component | Weight % |
|---|---|
| Sunflower Seed Oil | 10.00 |
| Glycerin | 10.00 |
| Maleated Soybean Oil | 5.00 |
| Silicone Urethane | 1.00 |
| Polyglycero-4 Oleate | 1.00 |
| Sodium C14-16 Olefin Sulfonate | 15.00 |
| Sodium Lauryl Ether Sulphate (25% active) | 15.00 |
| Cocoamidopropylbetaine | 15.00 |
| DC 1784 ® (Silicone Emulsion 50%) | 5.00 |
| Polyquaternium-11 | 1.00 |
| Myrtucommulone C | 0.01 |
| Fragrance (20% Limonene) | 0.70 |
| Water | To 100 |

Example 6

An illustrative toilet bar formula incorporating Lapachol is listed below.

| Component | Weight % |
|---|---|
| Sodium Soap (85/15 Tallow/Coconut) | 77.77 |
| Inventive compound 5a | 3.50 |
| Dimethicone | 2.00 |
| Sodium Chloride | 0.77 |
| Titanium Dioxide | 0.40 |
| Ethylene Brassylate | 1.50 |
| Disodium EDTA | 0.02 |
| Sodium Etidronate | 0.02 |
| Lapachol | 0.024 |
| Water | To 100 |

Example 7

A shampoo composition with thymoquinone is described below for illustrative purposes.

| Component | Weight % |
|---|---|
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| Glycerin | 12.00 |
| Thymoquinone | 1.50 |
| Ethylene Glycol Distearate | 1.50 |
| Cocomonoethanolamide | 0.80 |
| Cetyl Alcohol | 0.60 |
| Polyquaternium-10 | 0.50 |
| Dimethicone | 1.00 |
| Zinc Pyridinethione | 1.00 |
| Sodium Citrate | 0.40 |
| Citric Acid | 0.39 |
| Sodium Xylene Sulfonate | 1.00 |
| Fragrance (10% Limonene) | 0.40 |
| Sodium Benzoate | 0.25 |
| Kathon CG ® | 0.0008 |
| Benzyl Alcohol | 0.0225 |
| Water | To 100 |

Example 8

This Example illustrates an antiperspirant formula incorporating thymoquinone and lapachol in combination.

| Component | Weight % |
|---|---|
| (Isotridecyloxy)propionic acid (branched) | 2.0 |
| Cyclopentasiloxane | 37.0 |
| Dimethicone | 20.0 |
| Aluminum Zirconium Trichlorohydrex Glycinate | 15.0 |
| Thymoquinone and Lapachol (1:1 wt ratio) | 5.0 |
| $C_{18}$-$C_{36}$ Acid Triglyceride | 5.0 |
| Microcrystalline Wax | 3.0 |
| Glycerin | 8.0 |
| Silica | 2.5 |
| Dimethicone Crosspolymer | 1.0 |
| Ethylene Brassylate | 0.5 |
| Disodium EDTA | 0.4 |
| Butylated Hydroxytoluene | 0.3 |
| Citric Acid | 0.3 |

Example 9

This example describes a sunburn treatment composition including the DNA repair quinone which is myrtucommulone C.

| Component | Weight % |
|---|---|
| Cocoa Butter | 30.0 |
| Shea Butter | 18.0 |
| Jojoba Oil | 15.5 |
| Petrolatum | 15.0 |
| Stearic Acid | 6.0 |
| Magnesium Sulphate Pentahydrate | 3.0 |
| Zinc Oxide | 1.9 |
| Myrtucommulone C | 1.0 |
| Water | to 100 |

Example 10

Two cosmetic compositions were prepared, one containing lapachol (denoted RGN 1538) and the other containing myrtucommulone C (denoted RGN 1518) as active ingredients, and the stabilities of the active ingredients in these compositions were evaluated.

| Sample Name RGN 1538 | Specification | Actual | % Change Difference | % of original |
|---|---|---|---|---|
| Time 0 (Mar. 16, 2017) | 0.25 | 0.25 | 0% | 100% |
| RT 2 Weeks | 0.25 | 0.213 | 15% | 85% |
| 40° C., 2 weeks | 0.25 | 0.243 | 3% | 97% |
| 50° C., 2 weeks | 0.25 | 0.251 | 0% | 100% |
| −5° C., 2 weeks | 0.25 | 0.252 | −1% | 101% |
| F/T, 2 week | 0.25 | 0.21 | 16% | 84% |
| RT, 4 Weeks | 0.25 | 0.198 | 21% | 79% |
| 40° C., 4 weeks | 0.25 | 0.25 | 0% | 100% |
| 50° C., 4 weeks | 0.25 | 0.25 | 0% | 100% |
| −5° C., 2 weeks | 0.25 | 0.252 | −1% | 101% |
| Cycle 3X | 0.25 | 0.183 | 27% | 73% |
| RT, 6 Weeks | 0.25 | 0.178 | 29% | 71% |
| 40° C., 6 weeks | 0.25 | 0.252 | −1% | 101% |
| −5° C., 6 weeks | 0.25 | 0.252 | −1% | 101% |
| RT, 8 Weeks | 0.25 | 0.178 | 29% | 71% |
| 40° C., 8 weeks | 0.25 | 0.252 | −1% | 101% |
| −5° C., 8 weeks | 0.25 | 0.249 | 0% | 100% |
| RT, 12 Weeks | 0.25 | 0.146 | 42% | 58% |
| 40° C., 12 weeks | 0.25 | 0.254 | −2% | 102% |
| −5° C., 12 weeks | 0.25 | 0.251 | 0% | 100% |

The components of the RGN1538 compositions were as follows: caprylic/capric triglyceride, 15% by weight; hydroxyethyl acrylate/sodium acryloyldimethyl taurate copolymer, 0.5% by weight; polyacrylate crosspolymer-6, 0.5%, by weight; water, 77.75% by weight; glycerin, 5.0% by weight; phenoxyethanol, 0.9% by weight; ethylhexylglycerin, 0.1% by weight; and RGN1538, 0.25% by weight.

| Sample Name RGN 1518 | Specification | Actual | % Change Difference | % of original |
|---|---|---|---|---|
| Time 0 (Mar. 17, 2017) | 0.096 | 0.091 | 5% | 95% |
| RT, 2 Weeks | 0.096 | 0.089 | 7% | 93% |
| 40° C., 2 weeks | 0.096 | 0.088 | 8% | 92% |
| 50° C., 2 weeks | 0.096 | 0.089 | 7% | 93% |
| −5° C., 2 weeks | 0.096 | 0.087 | 9% | 91% |
| F/T, 2 week | 0.096 | 0.092 | 4% | 96% |
| RT, 4 Weeks | 0.096 | 0.087 | 9% | 91% |
| 40° C., 4 weeks | 0.096 | 0.088 | 8% | 92% |
| 50° C., 4 weeks | 0.096 | 0.092 | 4% | 96% |
| −5° C., 2 weeks | 0.096 | 0.088 | 8% | 92% |
| Cycle 3X | 0.096 | 0.091 | 5% | 95% |
| RT, 6 Weeks | 0.096 | 0.09 | 6% | 94% |
| 40° C., 6 weeks | 0.096 | 0.089 | 7% | 93% |
| −5° C., 6 weeks | 0.096 | 0.087 | 9% | 91% |
| RT, 8 Weeks | 0.096 | 0.088 | 8% | 92% |
| 40° C., 8 weeks | 0.096 | 0.088 | 8% | 92% |
| −5° C., 8 weeks | 0.096 | 0.092 | 4% | 96% |
| RT, 12 Weeks | 0.096 | 0.096 | 0% | 100% |
| 40° C., 12 weeks | 0.096 | 0.098 | −2% | 102% |
| −5° C., 12 weeks | 0.096 | 0.095 | 1% | 99% |

The components of the RGN1518 compositions were as follows: caprylic/capric triglyceride, 15% by weight; hydroxyethyl acrylate/sodium acryloyldimethyl taurate copolymer, 0.5% by weight; polyacrylate crosspolymer-6, 0.5%, by weight; water, 77.90% by weight; glycerin, 5.0% by weight; phenoxyethanol, 0.9% by weight; ethylhexylglycerin, 0.1% by weight; and RGN1518, 0.1% by weight.

Acceptable degradation of active compounds at the accelerated temperature conditions (40° C., 50° C., −5° C.) is 20% or 80% of original. The compounds RGN1518 and RGN1538 met this criteria at these temperatures at the two-, four-, six-, eight-, and 12-week time points.

Results from these tests show that the active ingredient is stable over a period of twelve weeks at varying accelerated temperature conditions. Thus, active ingredients should remain in the formulation and not breakdown.

Example 11

Lastly a repeat insult patch test (RIPT) was performed using the two cosmetic compositions described above. About fifty human volunteers were involved for each cosmetic composition (50 for RGN1518 and 52 for RGN1538).

Methods

Fifty-seven subjects, male and female, ranging in age from 20 to 75 years were selected to evaluate each cosmetic composition. Fifty-two subjects completed the study in each case. The remaining subjects discontinued their participation for various reasons, which were unrelated to the application of the test material.

(i) Inclusion Criteria

The following criteria were used to include subjects in the tests:

a. Male and female subjects, age 16[a] to 79 years.

[a] With parental or guardian consent b. Absence of any visible skin disease which might be confused with a skin reaction from the test material.

c. Prohibition of use of topical or systemic steroids and/or antihistamines for at least seven days prior to study initiation.

d. Completion of a medical history form and the understanding and signing of an Informed Consent form.

e. Considered reliable and capable of following directions.

(ii) Exclusion Criteria a. Ill-health.

b. Under a doctor's care or taking medication(s) which could influence the outcome of the study.

c. Females who are pregnant or nursing.

d. A history of adverse reactions to cosmetics or other personal care products.

The upper back between the scapulae served as the treatment area. Approximately 0.2 g of the test material, or an amount sufficient to cover the contact surface, was applied to a 1"×1" absorbent pad portion of a clear adhesive dressing. This was then applied to the appropriate treatment site to form a semi-occlusive patch.

(iii) Induction Phase

Patches were applied three (3) times per week (e.g., Monday, Wednesday, and Friday) for a total of nine (9) applications. The site was marked to ensure the continuity of patch application. Following supervised removal and scoring of the first Induction patch, participants were instructed to remove all subsequent Induction patches at home, twenty-four hours after application. The evaluation of this site was made again just prior to re-application. If a participant was unable to report for an assigned test day, one (1) makeup day was permitted. This day was added to the Induction period.

(iv) Induction Phase

With the exception of the first supervised Induction Patch reading, if any test site exhibited a moderate (2-level) reaction during the Induction Phase, application was moved to an adjacent area. Applications were discontinued for the remainder of this test phase, if a moderate (2-level) reaction was observed on this new test site. Applications would also be discontinued if marked (3-level) or severe (4-level) reactivity was noted.

Rest periods entailed one day following each Tuesday and Thursday removal, and two days following each Saturday removal.

(v) Challenge Phase

Approximately two (2) weeks after the final induction patch application, a challenge patch was applied to a virgin test site adjacent to the original Induction patch site, following the same procedure described for Induction. The patch was removed and the site scored at the clinic Day 1 and Day 3 post-application.

The formation of erythema and/or additional dermal sequelae were the criteria for evaluating the performance of the cosmetic compositions. Erythema was scored numerically according to the key below. If present, additional dermal sequelae were indicated by the appropriate letter code and a numerical value for severity.

| Number | Meaning | Letter(s) | Meaning |
|---|---|---|---|
| 0 | No visible skin reaction | E | Edema |
| 0.5 | Barely perceptible | D | Dryness |
| 1 | Mild | S | Staining |
| 2 | Moderate | P | Papules |
| 3 | Marked | V | Vesicles |
| 4 | Severe | B | Bullae |
|  |  | U | Ulceration |
|  |  | Sp | Spreading |

Results

There were no adverse events, amendments, or deviations. The results from the tests showed that the active ingredients do not cause any skin irritation or dermal sensitization on human subjects.

While the present compositions and methods have been described with reference to the specific variations thereof, it should be understood by those skilled in the art that various changes may be made and equivalents may be substituted without departing from the true spirit and scope of the compositions and methods described herein. In addition, many modifications may be made to adapt a particular situation, material, composition of matter, process, process step or steps, to the objective, spirit and scope of the compounds and methods described herein. All patents and publications cited above are hereby incorporated by reference.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for treating erythema, sunburn, signs of ageing, or a combination thereof in mammals in need thereof, comprising topically applying to the skin or hair of the mammals a cosmetic composition comprising a quinone having the structural formula:

Formula III

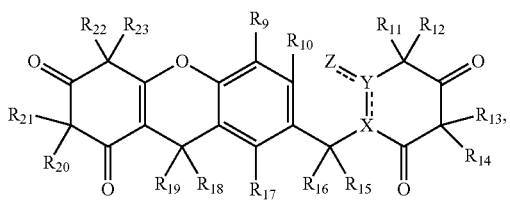

in amounts ranging from 0.001% to 10% by weight of the cosmetic composition, wherein $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, and $R_{23}$ are independently hydrogen, unsubstituted C1-C10 alkyl, substituted C1-C10 alkyl, hydroxyl, =O, substituted C1-C10 carbonyl, or unsubstituted C1-C10 carbonyl, thiol, halogen, aryl, substituted aryl, heteroaryl, substituted heteroaryl, alkoxy, substituted alkoxy, aroxy, substituted aroxy, alkylthio, substituted alkylthio, arylthio, substituted arylthio, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic; and wherein X and Y are independently carbon (C) or CH; Z is hydroxyl or oxygen; and the dashed line between X and Y, and between Y and Z shows the presence or absence of a bond, depending on the valency of X, Y, and Z.

2. The method according to claim 1 wherein the signs of ageing comprise fine lines and wrinkles.

3. The method according to claim 1 wherein the signs of ageing comprise lack of skin firmness.

4. The method according to claim 1 wherein the signs of ageing comprise reduction of skin luminescence.

5. The method according to claim 1 wherein the signs of ageing comprise lack of skin smoothness.

6. The method according to claim 1 wherein the signs of ageing comprise lack of skin elasticity.

7. The method according to claim 1 wherein the signs of ageing comprise formation of age spots.

8. The method according to claim 1 wherein the signs of ageing comprise blotching.

9. The method according to claim 1 wherein the signs of ageing comprise sallowness.

10. The method according to claim 1 wherein the signs of ageing comprise uneven pigmentation.

11. The method according to claim 1 wherein the signs of ageing comprise spider veins.

12. The method according to claim 1 wherein the signs of ageing comprise thinning and loss of hair.

13. The method according to claim 1 wherein the signs of ageing comprise lack of hair lustre or shine.

14. The method according to claim 1 wherein the signs of ageing comprise hair with split ends.

15. The method of claim 1, wherein for Formula III, (I) R9 is substituted C1-C10 carbonyl; (ii) R10 is hydroxyl; (iii) X is carbon (C) or CH, Y is carbon (C), Z is hydroxyl, the dashed line between X and Y is a bond, and the dashed line between Y and Z is absent; (iv) R17 is hydroxyl; and/or (v) R11, R12, R13, R14, R15, R16, R18, R19, R20, R21, R22, and R23 are independently hydrogen, substituted C1-C10 alkyl, or unsubstituted C1-C10 alkyl.

16. The method of claim 15 wherein for Formula III, R11, R12, R13, R14, R20, R21, R22, and R23 are unsubstituted C1-C5 alkyl; and R15 and R18 are hydrogen, R16 and R19 are substituted C1-C5 alkyl.

17. The method of claim 16, wherein for Formula III, R11, R12, R13, R14, R20, R21, R22, and R23 are methyl; R15 and R18 are hydrogen.

18. The method of claim 15, wherein for Formula III, R16 and R19 are isopropyl.

19. The method of claim 15, wherein Formula III is

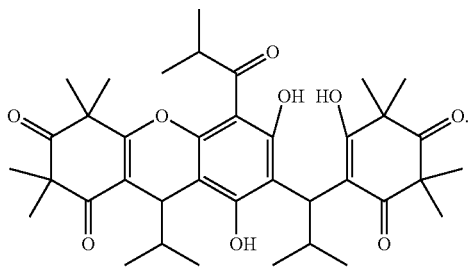

20. The method of claim 1, wherein the composition further comprises one or more sunscreens selected from the group consisting of 2-ethylhexyl p-methoxycinnamate, 4,4'-t-butyl methoxydibenzoylmethane, octylsalicylate, tetraphthalylidene dicamphor sulfonic acid, benzophenone-3, microfine titanium dioxide, microfine zinc oxide and mixtures thereof; surfactants selected from the group consisting of anionic, nonionic, cationic, and amphoteric type; a sunless tanning agent which is dihydroxy acetone; desquamation agents selected from the group consisting of glycolic acid, lactic acid, salicylic acid, retinoic acid, retinol and mixtures thereof, and including salt forms thereof; antiperspirants selected from the group consisting of metal salts of aluminum, zinc, zirconium and zirconium aluminum mixtures of sulfates, chlorides, chlorohydroxides, tetrachlorohydrex glycinates, alums, formates, lactates, benzyl sultanates, succinates, and phenol sultanates; colorants selected from pigments and dyes and/or preservatives selected from the group consisting of methylchloroisothiazolinone and methylisothiazolinone combinations, phenoxyethanol, methyl paraben, propyl paraben, imidazolidinyl urea, sodium dehydroacetate and benzyl alcohol.

21. A method for treating erythema in mammals in need thereof, comprising topically applying to the skin or hair of the mammals a cosmetic composition comprising a quinone having the structural formula:

Formula III

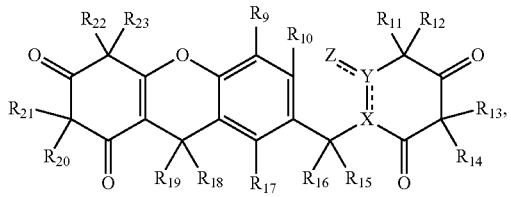

in amounts ranging from 0.001% to 10% by weight of the cosmetic composition, wherein $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, and $R_{23}$ are independently hydrogen, unsubstituted C1-C10 alkyl, substituted C1-C10 alkyl, hydroxyl, =O, substituted C1-C10 carbonyl, or unsubstituted C1-C10 carbonyl, thiol, halogen, aryl, substituted aryl, heteroaryl, substituted heteroaryl, alkoxy, substituted alkoxy, aroxy, substituted aroxy, alkylthio, substituted alkylthio, arylthio, substituted arylthio, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic; and wherein X and Y are independently carbon (C) or CH; Z is hydroxyl or oxygen; and the dashed line between X and Y, and between Y and Z shows the presence or absence of a bond, depending on the valency of X, Y, and Z.

* * * * *